US00PP33032P2

(12) United States Plant Patent
Hansen

(10) Patent No.: US PP33,032 P2
(45) Date of Patent: May 4, 2021

(54) **X *MANGAVE* PLANT NAMED 'FOXY LADY'**

(50) Latin Name: **x *Mangave* times *Agave***
Varietal Denomination: Foxy Lady

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 112 days.

(21) Appl. No.: 16/602,783

(22) Filed: Nov. 26, 2019

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new and unique X *Mangave* plant named 'Foxy Lady' characterized by a compact mound of short, broad, fleshy, heavily-glaucous leaves with centers of silvery-colored with lavender undertones, developing irregular smoky-purple spots and stripes in high ultraviolet light exposure. The variegated creamy-white margin develops spots of purplish-pink and contrasts with the orangish brown sharp tip of the teeth and short, sharp, terminal spines. 'Foxy Lady' is suitable for the garden landscape or as a potted plant around the garden or in the home.

1 Drawing Sheet

Botanical classification: hybrid; x *Mangave* times *Agave*. Variety denomination: 'Foxy Lady'.

STATEMENT REGARDING PRIOR DISCLOSURES UNDER 37 CFR 1.77(B)(6)

No plants of x *Mangave* 'Foxy Lady' have been sold, in this country or anywhere in the world under any name, nor has any disclosure of the new plant been made, more than one year prior the filing date of this application.

BACKGROUND OF THE INVENTION

The present invention relates to the new and distinct X *Mangave* hybrid plant, x *Mangave* 'Foxy Lady' discovered by the inventor at a wholesale perennial nursery in Zeeland, Mich., USA as a whole plant mutation found in a batch of tissue culture propagated plantlets of x *Mangave* 'Silver Fox' U.S. Plant Pat. No. 29,642. The mutation was discovered on Feb. 18, 2018. Through trials at the same nursery the plant was originally assigned the code 18-SP-MANG-640 until ultimately assigned the new cultivar name. The new plant has been successfully asexually propagated initially by division at the same nursery in Zeeland, Mich. Removal of basal offshoots and sterile shoot tip tissue culture have been found to produce stable and identical plants that maintain all the unique characteristics of the original plant.

BRIEF SUMMARY OF THE INVENTION

X *Mangave* 'Foxy Lady' differs from its parents as well as all other *Manfreda, Agave* and x *Mangave* known to the applicant. Compared with the sport parent the foliage of the new plant has a broad creamy margin. The most similar non-variegated x *Mangave* known cultivars are: x *Mangave* 'Catch a Wave' U.S. Plant Pat. No. 29,723. 'Purple People Eater' U.S. Plant Pat. No. 29,494 and 'Tooth Fairy' co-pending U.S. Plant Pat. No. 29,599. Compared with 'Catch a Wave' the new plant has flatter leaves that have a more glaucous blue overtone with a creamy margin. Compared to 'Tooth Fairy' the new plant has more arching leaves with more glaucous blue overtone, and the marginal teeth are more glaucous blue colored and not as large.

The most similar variegated x *Mangave* known to the inventor are: 'Navajo Princess' U.S. Plant Pat. No. 31,136, 'Snow Leopard' U.S. Plant Pat. No. 31,137, 'Kaleidoscope' U.S. Plant Pat. No. 28,614. 'Navajo Princess' has longer leaves with smaller teeth and green leaf centers. 'Snow Leopard' has longer and narrower leaves with darker green leaf centers and lighter white margins with much smaller teeth. 'Kaleidoscope' has longer narrower leaves with dark green centers and much smaller teeth more yellowish margins with cherry-red tinting. All of these comparison variegated x *Mangave* have thinner foliage.

The new plant, 'Foxy Lady', is unique from all of the above cultivars and all *Agave*, X *Mangave* and *Manfreda* known to the inventor by the following combined traits:

1. Compact mound of short, broad, fleshy, heavily glaucous foliage;
2. Foliage center develops light, irregular, smoky-purple spots with high ultraviolet light exposure frequently-overlapping throughout upper surface;
3. Marginal teeth are large, with the tips short, sharp, orangish-brown;
4. The silvery leaves with lavender undertone have clean creamy-white margins with pinkish-purple spotting;
5. The leaves have teeth imprints from the enrolled developing foliage;
6. Moderate growth rate.

BRIEF DESCRIPTION OF THE DRAWING

The photograph of x *Mangave* 'Foxy Lady' demonstrates the overall appearance of the new plant including the unique traits as a two-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
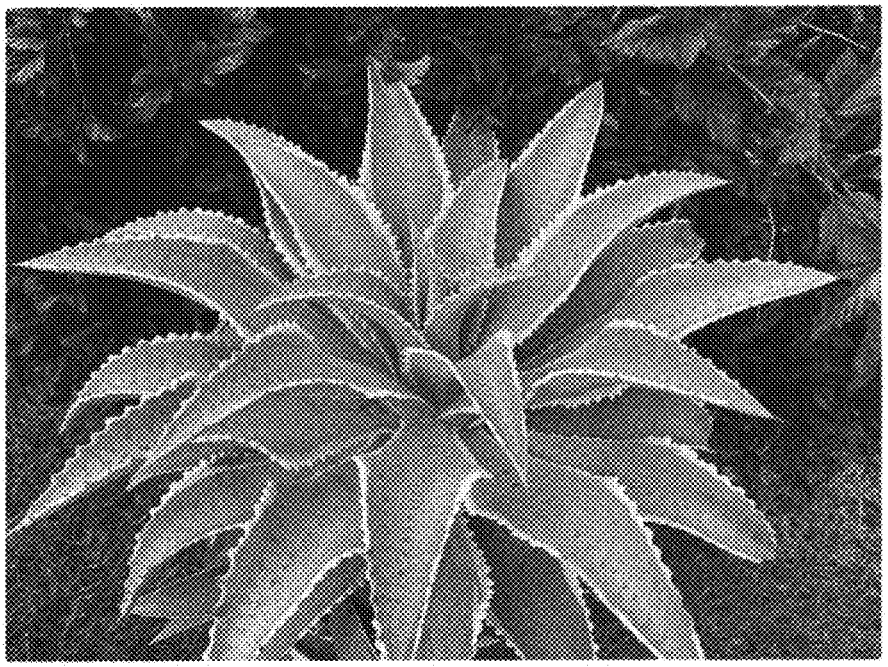
FIG. 1 shows a side view of the new plant grown in a container with foliage color, pronounced marginal teeth and apical spines and creamy-white variegation with pinkish-purple spotting.
Figure 2:
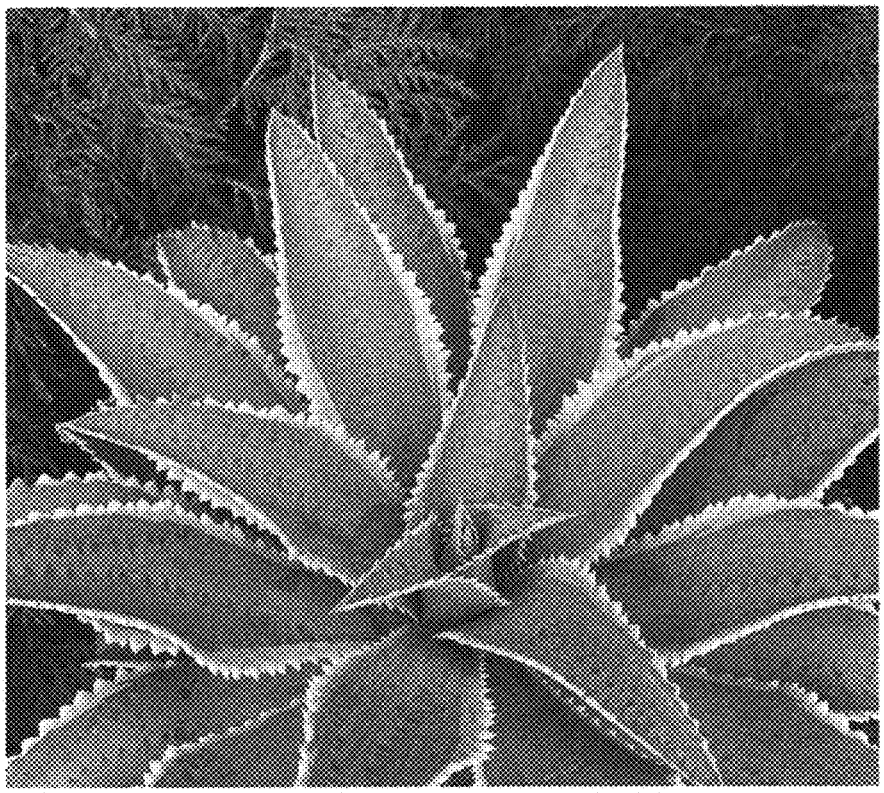
FIG. 2 shows a view from above of the new plant with irregular purple spotting and large marginal teeth, teeth imprints and creamy-white variegation with pinkish-purple spotting.

The following descriptions and color references are based on the 2015 edition of The Royal Horticultural Society Colour Chart except where common dictionary terms are used. The new plant, X *Mangave* 'Foxy Lady', has not been observed under all possible environments. The phenotype may vary slightly with different environmental conditions, such as temperature, light, fertility, moisture and maturity levels, but without any change in the genotype. The following observations and size descriptions are of a two-year old plant in a commercial wholesale greenhouse in Zeeland, Mich. with supplemental water and fertilizer as needed.

Parentage: Whole plant mutation of x *Mangave* 'Silver Fox';

Propagation: Removal of basal offshoots and sterile shoot tip tissue culture;

Time to initiate roots from tissue culture: About 21 days;

Growth rate: Moderate; faster than typical *Agave;*

Crop time: About 14 to 18 weeks to finish in a 3.8 liter container from a 35 mm tissue culture growing at about 24° C.;

Rooting habit: Fleshy, lightly branching, with roots up to 30.0 cm long;

Root color: Nearest RHS 158C;

Plant shape and habit: Succulent herbaceous perennial with basal rosettes of about 50 leaves radially emerging outwardly from central stem, producing a radially-symmetrical, rounded mound;

Plant size: Foliage height about 20.0 cm tall from soil line to the top of the leaves and about 38.0 cm wide at the widest point slightly below soil line in container;

Foliage description: Lanceolate; arcuate distally; simple; margins coarsely dentate with short stiff spines, thick and fleshy; asperous adaxial and abaxial; teeth about 4.0 mm long and spaced average of about 4.0 mm to 6.0 mm apart; apex acute with terminal spine about 6.0 mm long; base truncate and slightly attenuate; sessile; slightly longitudinally conduplicate; bi-laterally symmetrical; with irregular purple spots and stripes; about 38 leaves per plant;

Leaf size: To about 20.0 cm long, about 5.0 cm wide approximately two-thirds toward apex and about 10.0 mm thick at middle base; average about 18.0 cm long, 4.2 cm wide and 9.0 mm thick; creamy variegated margin to about 12.0 mm wide, average about 10.0 mm;

Foliage fragrance: None observed;

Leaf blade color:

*Adaxial* (*young*).—Nearest blend between RHS 189B and RHS 191B, with irregular spots and stripes intensifying with ultraviolet light exposure to nearest blend of RHS N186C and RHS N187B, variegated margin nearest RHS NN155B with irregular spots and blotches of nearest RHS 186C.

*Abaxial* (*young*).—Nearest blend between RHS 189B and RHS 191B without noticeable spots in center portion, margin nearest RHS NN155B with irregular spots and blotches between RHS 186C and RHS 186D.

*Adaxial* (*mature*).—Blend between RHS 188B and RHS 191B with spots and stripes intensifying with ultraviolet light exposure nearest blend between RHS N187A and RHS 187A, with margin of nearest RHS NN155C also having irregular spots and blotches nearest RHS 186C.

*Abaxial* (*mature*).—Nearest RHS 189C without noticeable spots in center portion, margin nearest RHS NN155C with irregular spots and blotches of between RHS 186C and RHS 186D.

Teeth spine color: Sharp apex nearest RHS 200B and 1.0 mm to 2.0 mm below nearest RHS 175A;

Apical spine color: Nearest RHS 200B;

Petiole: Leaves sessile;

Veins: Parallel; not distinct abaxial or adaxial;

Inflorescence: Not yet observed.

Flower description: Not yet observed;

Disease resistance: X *Mangave* 'Foxy Lady' has not been observed to be resistant to diseases beyond that which is normal for X *Mangave, Agave* or *Manfreda*. The new plant is xeromorphic and survives well with minimal water once established. The new plant is hardy at least in USDA zone 10. Full extent of winter hardiness has not been tested.

It is claimed:

1. A new and distinct cultivar of ornamental X *Mangave* plant named 'Foxy Lady' as herein described and illustrated.

* * * * *